(12) United States Patent
Booth (10) Patent No.: US 6,576,033 B1
(45) Date of Patent: Jun. 10, 2003

(54) FILTER FOR USE IN MEDICAL PROCEDURES

(75) Inventor: Charles S. Booth, Livonia, MI (US)

(73) Assignee: Pall Corporation, East Hills, NY (US)

(*) Notice: Subject to any disclaimer, the term of this patent is extended or adjusted under 35 U.S.C. 154(b) by 0 days.

(21) Appl. No.: 09/856,977

(22) PCT Filed: Nov. 22, 1999

(86) PCT No.: PCT/US99/28204

§ 371 (c)(1),
(2), (4) Date: Aug. 10, 2001

(87) PCT Pub. No.: WO00/32296

PCT Pub. Date: Jun. 8, 2000

Related U.S. Application Data (60) Provisional application No. 60/137,497, filed on Jun. 4, 1999, and provisional application No. 60/110,229, filed on Nov. 30, 1998.

(51) Int. Cl.[7] ............................................. B01D 46/12
(52) U.S. Cl. ...................... 55/485; 55/486; 55/522; 55/524; 55/527; 428/36.1; 428/246; 428/284; 604/23; 604/24; 604/25; 604/26; 604/27; 604/28; 604/30; 604/31; 604/32; 604/33; 604/34; 604/35; 604/41
(58) Field of Search ...................... 55/485, 486, 487, 55/488, 522, 524, 527, 528; 428/36.1, 246, 284, 298; 604/23–28, 30–35, 41

(56) References Cited

U.S. PATENT DOCUMENTS

| 3,596,441 A | 8/1971 | Lundahl |
| 3,736,728 A | 6/1973 | Kleissler, Jr. |
| 3,858,572 A | 1/1975 | Binard et al. |
| 4,106,213 A | 8/1978 | Witte |
| 4,220,633 A | 9/1980 | Pirsh |
| 4,324,574 A * | 4/1982 | Fagan .......................... 55/381 |

(List continued on next page.)

FOREIGN PATENT DOCUMENTS

| DE | 196 06 718 A1 | 8/1997 |
| EP | 0 960 644 A1 | 12/1999 |
| WO | WO 97/30772 A1 | 8/1997 |
| WO | WO 98/31451 A1 | 7/1998 |

OTHER PUBLICATIONS

"Table 5: Chemicals, Exposure Limits and Associate Health Effects" p. 12, as well as pp. 16 & 17 in *Surgical Smoke: What We Know Today*, copyright 1996, Valleylab, Inc., Boulder, CO.

"Amire Breakthrough Volumes on Tenax TA," SIS Tenax TA; http://www.sisweb.com/index/reference/tenamine.htm May 28, 1999.

Technical Bulletin "Environment Tobacco Smoke Breakthrough," AQF Technologies, 2 pgs, copyright 1998, and also including "Typical Property Sheet AQF© Media: 2750," 1 pg.

"The First 'Connect It and Forget It' Evacuator for Laparoscopic Smoke Removal." 1 pg., Undated.

*Primary Examiner*—David A. Simmons
*Assistant Examiner*—Minh-Chau T. Pham
(74) *Attorney, Agent, or Firm*—Leydig, Voit & Mayer, Ltd.

(57) ABSTRACT

A smoke filter device for use in medical procedures such as laparoscopy is disclosed, the device comprising a filter housing having an inlet port and first and second side walls, the side walls comprising non-woven media, and a smoke filter capable of filtering smoke from gas, wherein the filter is disposed in the housing.

34 Claims, 7 Drawing Sheets

U.S. PATENT DOCUMENTS

| | | | |
|---|---|---|---|
| 4,382,440 A | * 5/1983 | Kapp et al. | 55/486 |
| 4,477,270 A | * 10/1984 | Tauch | 55/486 |
| 4,487,606 A | 12/1984 | Leviton et al. | |
| 4,561,868 A | 12/1985 | von Reis et al. | |
| 4,619,672 A | * 10/1986 | Robertson | 55/485 |
| 4,661,092 A | 4/1987 | Popovich et al. | |
| 4,702,940 A | * 10/1987 | Nakayama et al. | 55/487 |
| 4,735,603 A | 4/1988 | Goodson et al. | |
| 4,816,328 A | * 3/1989 | Saville et al. | 55/487 |
| 4,874,586 A | 10/1989 | Szymanski et al. | |
| 4,877,433 A | * 10/1989 | Oshitari | 55/487 |
| 4,894,074 A | 1/1990 | Mizrah et al. | |
| 4,957,518 A | * 9/1990 | Brassell | 55/385.4 |
| 5,098,375 A | 3/1992 | Baier | |
| 5,108,474 A | 4/1992 | Riedy et al. | |
| 5,176,629 A | 1/1993 | Kullas et al. | |
| 5,199,944 A | 4/1993 | Cosmescu | |
| 5,205,850 A | 4/1993 | Jenrich et al. | |
| 5,288,299 A | 2/1994 | Yoshida et al. | |
| 5,294,236 A | 3/1994 | Baird | |
| 5,342,349 A | 8/1994 | Kaufman | |
| 5,507,847 A | 4/1996 | George et al. | |
| 5,578,000 A | 11/1996 | Greff et al. | |
| 5,647,881 A | 7/1997 | Zhang et al. | |
| 5,674,219 A | 10/1997 | Monson et al. | |
| 5,722,962 A | 3/1998 | Garcia | |
| 5,779,662 A | 7/1998 | Berman | |
| 5,814,012 A | 9/1998 | Fleenor et al. | |
| 5,874,052 A | 2/1999 | Holland | |

\* cited by examiner

FILTER FOR USE IN MEDICAL PROCEDURES

This application is a 35 U.S.C. §371 of PCT/US99/28204. This application claims the benefit of U.S. provisional patent applications 60/110,229, filed Nov. 30, 1998, and 60/137,497, filed Jun. 4, 1999, which are incorporated by reference.

TECHNICAL FIELD

This invention relates to a filter for use in medical procedures, more particularly, for use in laparoscopic or endoscopic surgery.

BACKGROUND OF THE INVENTION

During some medical procedures, e.g., laparoscopic and endoscopic surgery, a suitable gas is introduced into the abdominal cavity to inflate the abdomen. The inflation of the abdomen tends to separate the interior organs and to provide an enlarged cavity within which to perform the surgery. For example, one or more trocars can be used to puncture the abdomen, and insufflation gas can be passed through at least one of the trocar(s) to inflate the abdomen. One or more instruments involved in the surgery, e.g., a laparoscope, scalpel, laser and/or electrocautery device, can be inserted through the appropriate trocar(s) as needed.

When a particular procedure requires cutting of tissues and/or blood vessels, lasers, ultrasonic tissue fragmentation devices and electrocautery devices can be used as they are easily manipulated, and produce relatively clean cuts. Moreover, they have a cauterizing effect, thus limiting bleeding.

Once surgery is completed, the gas used to inflate the cavity is vented from the abdominal cavity. Additionally, since cutting with lasers, ultrasonic tissue fragmentation devices and electrocautery devices often produces vapor or "smoke," that can cloud or obstruct the surgeon's view of the operative site, the surgeon may vent gas (including smoke) during the surgery to remove the smoke from the abdominal cavity. For example, the surgeon may release a valve associated with a cannula communicating with one of the trocars and vent the smoke to the surrounding atmosphere. Alternatively, the smoke can be recirculated, e.g., withdrawn from one trocar and reintroduced into the abdominal cavity through another trocar.

However, the smoke can contain toxic, odiferous, and otherwise undesirable material (e.g., benzene, hydrogen cyanide, toluene, formaldehyde, carbon monoxide, viruses, bacteria, cells, and/or body fluids from diseased tissue of the patient) that, if released into the environment of the operating room, could expose the surgeon and the surgeon's staff to a health risk. Additionally, the release or recirculation of this smoke (that can, for example, contain bacteria and/or viruses) can subject the patient to the risk of additional contamination, e.g., via absorption through the peritoneum, or by entering the body at a location other than the abdominal cavity.

Attempts have been made to filter some of the gas passed from the abdominal cavity of the patient. However, these filters have suffered from a number of drawbacks. For example, some of the filters are bulky, and interfere with the surgeon's vision and/or the surgeon's ability to move in and around the surgical site. The filters may be easily plugged, fail to remove sufficient undesirable material and/or may require a labor intensive effort (possibly requiring numerous steps) to operate. Special equipment (e.g., instruments, valves and/or evacuators) may have to be utilized with the filters. Alternatively, or additionally, the filters may be unsuitable for use with adjustable gas flow rates and/or gas flow rates of about 1 liter/min or more at standard insufflation pressure.

The present invention provides for ameliorating at least some of the disadvantages of the prior art. These and other advantages of the present invention will be apparent from the description as set forth below.

SUMMARY OF THE INVENTION

In accordance with an embodiment of the instant invention, a filter device for gas(es), preferably gas vented from a patient's body cavity (e.g., during laparoscopic surgery) is provided comprising at least one flexible filter comprising a flexible filter element, wherein the filter device is arranged to allow gas to pass therethrough. For example, a surface of the flexible filter can provide a wall or side of the filter device, wherein gas passes from one surface of the flexible filter, through the filter, and through an opposing surface of the filter, wherein a wall or side of the filter device comprises the opposing surface of the filter.

In some embodiments, the filter device comprises a housing and at least one filter element, wherein at least a portion of the housing is flexible and allows gas to pass therethrough, the filter device being arranged to allow gas to pass through the filter element(s) and the flexible portion of the housing.

In another embodiment, the filter device comprises a housing and at least one filter element, wherein the filter element has an effective filtration area of at least about 12.9 $cm^2$ (at least about 2 $in^2$), the filter device being arranged to allow gas to pass through the filter element(s) and through a portion of the housing.

In some embodiments, at least a portion of the housing and/or the filter element is flexible. In other embodiments, the housing and the filter element are substantially inflexible.

In preferred embodiments, the filter device removes laparoscopic smoke and reduces odor as the gas passes through the device to the exterior of the housing.

Embodiments of the filter and filter device are suitable for use at any desirable constant or variable gas flow rate. Preferably, the filter device can be easily added to any suitable system (e.g., a system for use in laparoscopic surgery). In an embodiment, the filter device (that can be part of a set) allows one-handed gas flow adjustment.

Embodiments of the invention are particularly for use in surgical environments, especially for use in laparoscopic surgery, as they can allow the surgical procedure to be 5 completed more quickly and/or cost efficiently, e.g., by reducing the amount of valuable surgeon-, nurse-, technician- and/or operating room-time needed for the procedure. Time savings are particularly advantageous, since, for example, as of 1999, at least one study has estimated the value of time in the operating room during laparoscopic surgery as well over $120 per minute.

In accordance with the invention, a gas filter (preferably a smoke filter) comprises a retentive member, i.e., it retains at least one undesirable material such as at least one of microorganisms (e.g., bacteria), viruses, cells, body fluids, aerosols and liquid droplets, and allows at least a portion of the gas to pass through the retentive member, wherein the gas is depleted of at least some level of the undesirable material (s). The retentive member may also retain or reduce the passage therethrough of other undesirable material such as at least one of benzene, hydrogen cyanide, formaldehyde, and toluene, and/or the member may reduce the passage of odor therethrough. The smoke filter comprises at least one porous substrate of any suitable nature, e.g., a porous medium such as a fibrous web, a membrane, combinations thereof, and the like. Typically, at least a portion of the smoke filter is flexible.

Typically, the gas filter comprises at least one smoke filter element comprising a porous retentive substrate, preferably a porous retentive medium. The porous substrate can have any suitable physical dimensions and typically will be in sheet form having two opposing sides (e.g., a first side and an opposing second side) with a central portion therebetween, wherein the pores in the porous substrate will generally enable fluid communication between the first and second sides of the porous substrate. Typically, the gas filter comprises a smoke filter element comprising at least one hydrophobic membrane (preferably a hydrophobic microporous membrane) and/or at least one hydrophobic fibrous medium, through which the fluid (e.g., gas) to be treated passes. The element has two opposing sides (e.g., a first side and an opposing second side, in relation to a fluid to be treated wherein at least a portion of the gas is passed through the element), with a central portion therebetween. The pores in the element generally enable fluid communication between the two opposing sides (e.g., between the first and second sides) of the element.

The smoke filter can have any suitable pore structure, for example, a Dioctyl Phthalate (DOP) smoke penetration rating, or a pore rating (e.g., ability to remove particles of a given size to a specified degree, as evidenced, for example, by bubble point). The smoke filter can have a pore structure that is uniform, substantially uniform, or it can vary in a continuous, a discontinuous, or a stepwise manner. For example, the smoke filter can have a graded pore structure. In some embodiments, the smoke filter includes a plurality of elements and/or layers wherein individual elements and/or layers have different pore structures, e.g., different pore ratings. For example, the smoke filter can comprise a smoke filter element having a plurality of layers wherein at least two layers have different pore ratings.

The smoke filter can include additional elements, layers, or structures, which can also be membranes, or other porous media. For example, in some embodiments, the smoke filter can include additional components that have different structures and/or functions, e.g., at least one of prefiltration, odor-reduction, support, drainage, spacing and cushioning. In some embodiments wherein the smoke filter includes one or more additional elements, at least a portion of each of the additional elements is flexible.

As used herein, the term "smoke" includes gas (e.g., the 35 insufflation gas as well as some of the material and/or some of the by-products produced by the ablation of tissues and/or blood vessels (e.g., aerosols and droplets). Smoke can include additional material, such as at least one of bacteria and viruses.

BRIEF DESCRIPTION OF THE DRAWINGS

FIG. 7 is a top view (FIG. 7a) and a cross-sectional view (FIG. 7b, along line 7b–7b of FIG. 7a) of another embodiment of an assembled smoke filter device wherein the device includes a manifold including an inlet port.

SPECIFIC DESCRIPTION OF THE INVENTION

In accordance with an embodiment of the present invention, a gas filter device is provided comprising a gas filter adapted to filter smoke, the gas filter having a first surface and an opposing second surface, the device having at least one wall (typically a side wall) comprising at least a portion of the second surface of the gas filter, wherein at least the portion of the wall allows gas to pass therethrough, the gas filter comprising at least one porous filter element comprising a hydrophobic retentive member, wherein the gas filter device is arranged to allow gas to pass through the filter and through the portion of the wall. In some embodiments, at least a portion of the wall is flexible, and the filter device is arranged to allow gas to pass through the filter and through the flexible portion of the wall.

In an embodiment of the gas filter device, the gas filter comprises at least two gas filters (preferably at least two smoke filters), the first and second gas filters each having a first surface and an opposing second surface, the device having at least two side walls, the first side wall comprising at least a portion of the second surface of the first gas filter, the second side wall comprising at least a portion of the second surface of the second gas filter, wherein the gas filter device is arranged to allow gas to pass through the filters and through the portions of the side walls.

In accordance with an embodiment of the present invention, a gas filter device is provided comprising a filter housing having an interior cavity, the housing having at least one wall, wherein at least a portion of the wall allows gas to pass therethrough, and a gas filter capable of filtering smoke comprising at least one porous filter element, wherein the filter element comprises a hydrophobic retentive member, and the gas filter device is arranged to allow gas to pass through the smoke filter and through the portion of the wall of the housing. In one embodiment, the filter element has an effective filtration area of at least about 12.9 cm$^2$ (about 2 in$^2$). Preferably, the hydrophobic retentive member comprises a microorganism- and/or virus-retentive member. In one preferred embodiment, the filter housing has at least one side wall substantially comprising a non-woven medium that allows gas to pass therethrough.

In an embodiment, a smoke filter device comprises a smoke filter comprising at least one porous filter element comprising a hydrophobic retentive member, the filter element having an effective filtration area of at least about 12.9 cm$^2$ (about 2 in$^2$), wherein the smoke filter device is capable of filtering smoke for at least about 3 minutes of cumulative smoke with a reduction of gas flow of about 50% or less. The filter element can include at least a portion that is flexible. In another embodiment, the filter element is substantially inflexible.

Typically, the gas filter comprises a smoke filter including at least one additional element such as a prefilter element and/or an odor-reducing element that also allow gas to pass therethrough. In an embodiment, the smoke filter prevents the passage of bacteria therethrough.

In some embodiments, the gas filter device comprises a housing having at least first and second side walls, wherein at least a portion of each of the two side walls is flexible, and allows gas to pass therethrough, and at least first and second smoke filters, each smoke filter comprising at least one porous filter element, each porous filter element comprising a hydrophobic retentive member, wherein the device is arranged to allow a portion of gas to pass through the first smoke filter and the first side wall, and to allow a portion of gas to pass through the second smoke filter and the second side wall. In a preferred embodiment, the first and second smoke filters each include at least one additional element such as a prefilter element and/or an odor-reducing element. In some embodiments, the first and second side walls of the filter housing substantially comprise a non-woven medium that allows gas to pass therethrough.

In accordance with another embodiment of the invention, a smoke filter arrangement that allows gas to pass therethrough is provided comprising a first smoke filter, the first smoke filter comprising a first porous element comprising a hydrophobic retentive member, a prefilter element and/or an additional element comprising an odor-reducing medium; and a second smoke filter, the second smoke filter comprising a second porous filter element comprising a hydrophobic retentive member, a prefilter element and/or an additional element comprising an odor-reducing medium. In an embodiment, the retentive member also comprises a prefilter element, and the smoke filter(s) comprise a porous element comprising a hydrophobic retentive member/prefilter and an additional element comprising an odor-reducing medium.

In accordance with another embodiment of the invention, a smoke filter arrangement that allows gas to pass therethrough is provided comprising a first smoke filter, the first smoke filter comprising a first porous element comprising a hydrophobic retentive member; and a second smoke filter, the second smoke filter comprising a second porous filter element comprising a hydrophobic retentive member, wherein the smoke filter arrangement has an effective filtration area of at least about 12.9 cm$^2$ (about 2 in$^2$)

In some embodiments, a smoke filter device including the smoke filter arrangement comprises at least a first side wall and a second side wall, at least a portion of the first side wall and the second side being flexible and allowing gas to pass therethrough, wherein at least a portion of the first side wall comprises a surface of the first smoke filter, and wherein at least a portion of the second side wall comprises a surface of the second smoke filter.

Each of the components of the invention will now be described in more detail below, wherein like components have like reference numbers.

FIGS. 1–5 illustrate a perspective view of an assembled device (FIG. 1), an exploded view (FIGS. 2, 4 and 5) and a cross-sectional view (FIG. 3) of embodiments of a filter device according to the invention, wherein the device is arranged to allow gas (e.g., in the form of smoke) to enter the interior of the device, pass through the gas filter(s), and through a portion of the housing of the filter device. Typically, each gas filter (hereinafter referred to as a "smoke filter") includes a plurality of elements that allow gas to pass therethrough, e.g., a smoke filter element, as well as a prefilter element and/or an odor-reducing element.

In the illustrative embodiments shown in FIGS. 2–5, the smoke filter device 300 comprises filter housing 50, having first side wall 5, and second side wall 55, wherein at least a portion of each of the first and second side walls is flexible (e.g., pliable) and porous. The filter device 300 includes a filter arrangement 200 comprising a first smoke filter 100 and a second smoke filter 101, typically with a space 90 between the first smoke filter and the second smoke filter. The illustrated filter device also includes an inlet 75 including an inlet port, the filter device being arranged to allow gas to pass through the inlet, into the space 90 between the first and second smoke filter 100, 101, wherein a portion of the gas subsequently passes through the first smoke filter 100 and the first side wall 5, and another portion of the gas passes through the second smoke filter 101 and the second side wall 55.

Figure 7A:
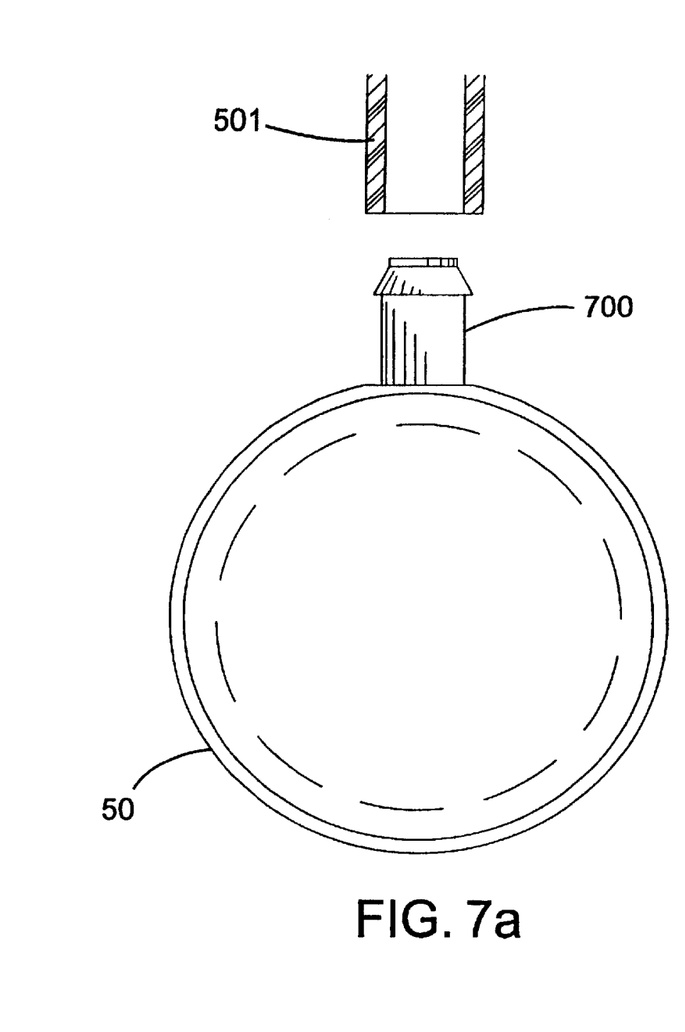
Figure 7B:
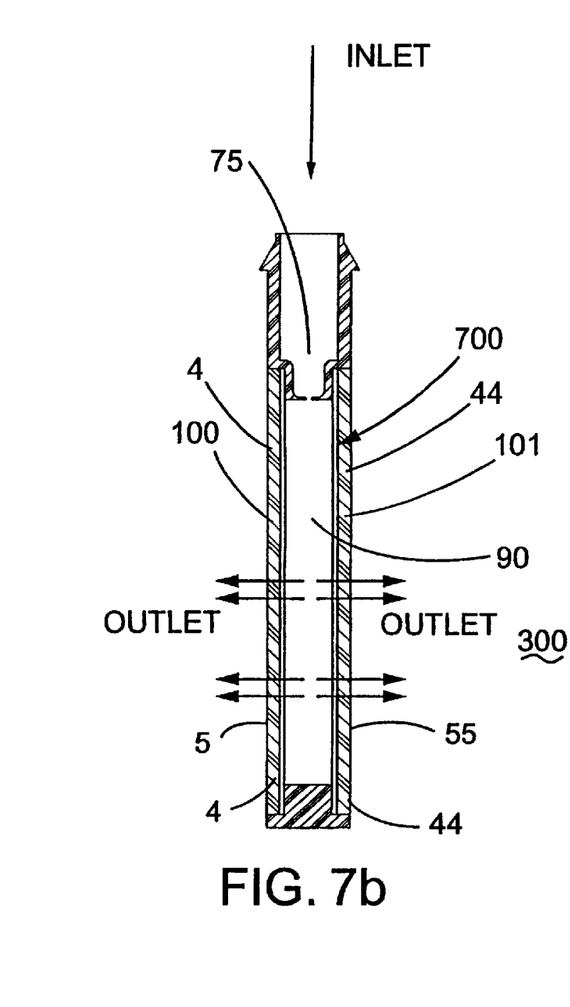

In the embodiment illustrated in FIGS. 7a and 7b, the filter device includes a manifold 700. As shown in FIG. 7b in the illustrated embodiment the manifold includes the inlet 75, allowing gas to pass through the manifold and the inlet, and into the space 90 between the first and second smoke filters 100 and 101, wherein a portion of the gas subsequently passes through the first smoke filter 100 and the first side wall 5, and another portion of the gas passes through the second smoke filter 101 and the second side wall 55.

The first and second smoke filters 100, 101, each comprise a porous smoke filter element 1, 11 comprising at least one hydrophobic retentive member. Preferably, the hydrophobic retentive member comprises a microorganism and/or virus retentive member. The hydrophobic retentive member typically comprises at least one membrane and/or at least one depth filter. Typically, the smoke filter includes additional elements such as a prefilter element and/or an odor-reducing element. In the embodiment illustrated in FIGS. 2 and 3, the first and second smoke filters also include a prefilter element 2, 22, and an odor-reducing element 3, 33, wherein the porous smoke filter element 1, 11 is interposed between the prefilter element 2, 22 and the odor-reducing element 3, 33. Alternatively, or additionally, the hydrophobic retentive member can also provide prefiltration.

Preferably, the smoke filter arrangement 200 is secured to the housing 50. For example, in accordance with the embodiments shown in FIGS. 3 and 7b, the first smoke filter 100 is sealed to a portion of the first side wall 5, and the second smoke filter 101 is sealed to a portion of the second side wall 55. The embodiment illustrated in FIG. 7b also shows portions of the first and second smoke filters sealed to a portion of the manifold 700.

Figure 4:
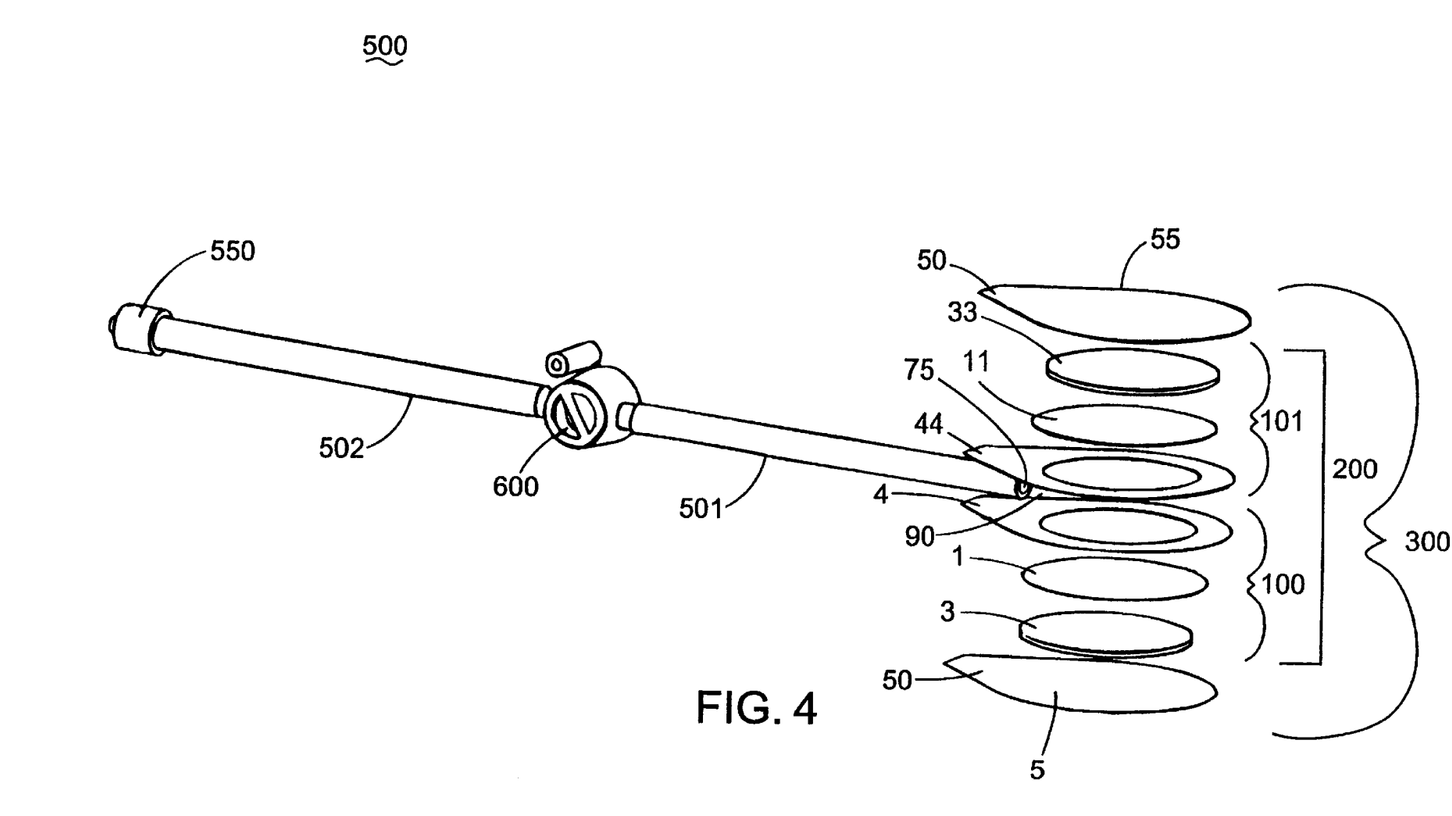
FIG. 4 is an exploded view of another embodiment of a smoke filter device including a smoke filter arrangement according to the present invention.
Figure 5:
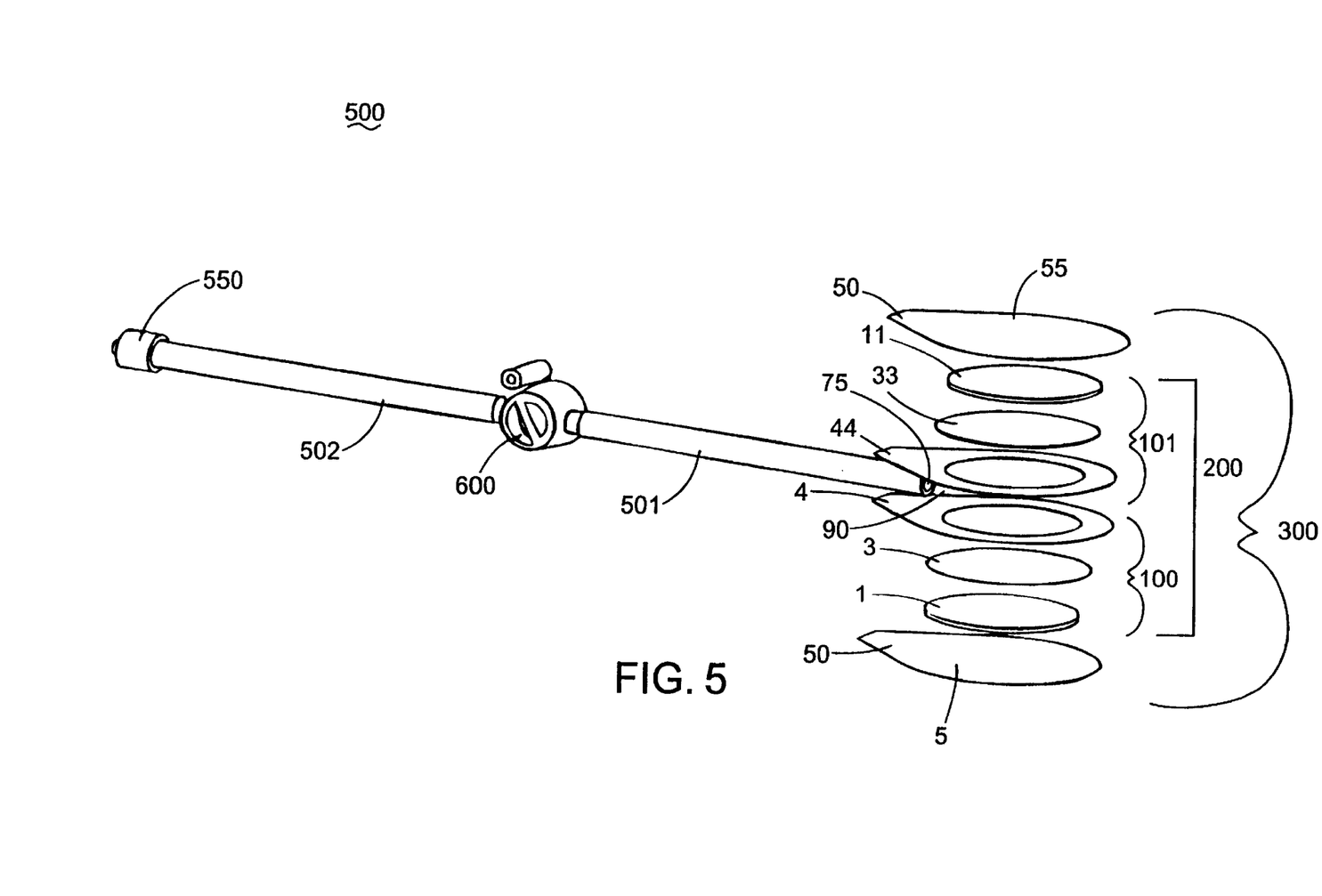
FIG. 5 is an exploded view of another embodiment of a smoke filter device including a smoke filter arrangement according to the present invention.

FIGS. 4 and 5 show other two other embodiments of the filter device 300, wherein the smoke filter includes a porous smoke filter element 1, 11 and an odor-reducing element 3, 33. In the embodiment shown in FIG. 4, the odor-reducing element 3, 33 is downstream of the porous smoke filter element 1, 11, and in the embodiment shown in FIG. 5, the odor-reducing element is upstream of the porous smoke filter element.

Figure 6:
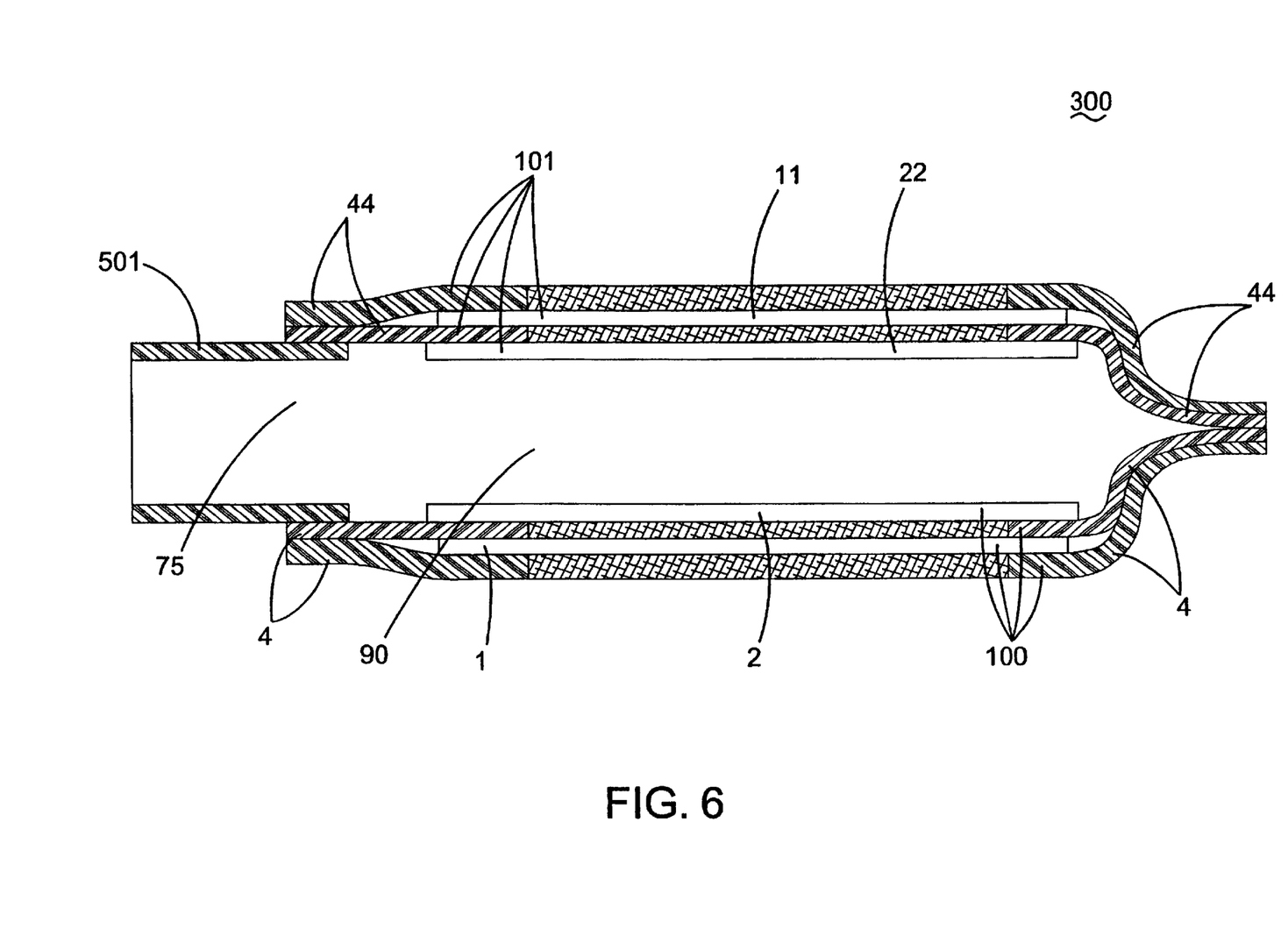
FIG. 6 is a cross-sectional view of another embodiment of a smoke filter device according to the invention wherein the device does not include a housing, and a portion of the first side wall of the device comprises a surface of the first smoke filter, and a portion of the second side wall of the device comprises a surface of the second smoke filter.

FIG. 6 illustrates a cross-sectional view of an embodiment of the filter device wherein the device lacks a housing, and the device is arranged to allow gas to enter the interior of the device, and pass through the gas filters to the exterior of the device.

The smoke filter device 300 can be utilized as part of a set, that can include additional components such as, but not limited to, at least one of a conduit, flow control device, and a connector. Typically, the set comprises a smoke filter device, at least one conduit, and at least one connector.

FIGS. 1, 2, 4, and 5 illustrate an embodiments of a set 500, comprising the filter device 300, a connector 550, first and second conduits 501, 502, and flow control device 600. In another embodiment (e.g., as shown in FIG. 7a) the set includes at least one connector between the first conduit 501, and the filter device 300. Suitable connectors include, but are not limited to, a universal fitting or coupler such as a luer fitting; a push-on fitting such as a barb type fitting, and the like.

Turning now to the individual components of the smoke filter device according to the embodiments of the invention, these components are compatible with the gas being utilized and, for those protocols that include producing smoke, these components are compatible with the smoke being produced in the protocol (e.g., laparoscopy, endoscopy, thoracoscopy, obstetrics-gynescopy), and can be produced from a variety of materials. In some embodiments, the components are compatible with one or more disinfection and/or sterilization protocols, including, for example, using ethylene oxide or gamma sterilization.

In those embodiments wherein the device includes a housing, the housing 50 can be of any suitable configuration and size. In a preferred embodiment, the housing is light weight. In an embodiment, the housing can be formed without the use of a mold. The housing can be, for example, generally teardrop shaped, round, oval, square, rectangular, or triangular. In the embodiment shown in FIG. 1, the housing 50 has a generally bag-like configuration, with first and second side walls, an open end, and a sealed end, wherein the open end is secured (e.g., sealed) to the inlet. In the embodiment shown in FIG. 7a, the housing 50 has a generally rounded configuration, with first and second side walls, wherein the side walls are secured (e.g., sealed) to the manifold 700. Typically, at least a portion of each of the first and second side walls 5, 55 is flexible. In some embodiments, at least a substantial portion (e.g., at least about 50% of the area) of each of the side walls is flexible, and substantially all of the housing can be flexible.

The filter device can include additional components, e.g., the housing can include a manifold 700 (FIGS. 7a and 7b), typically providing a common inlet flow path into interior of the device. In accordance with the embodiment illustrated in FIGS. 7a and, more particularly, 7b, at least a portion of each of first and second side walls 5, 55 is preferably flexible. The manifold can be flexible or substantially inflexible.

A variety of materials that allow gas to pass therethrough are suitable for the housing. Typically, the material has a low profile, low weight, and is compact. For example, the housing can comprise one or more screens (e.g., polyester or polypropylene) and/or one or more porous woven and/or non-woven materials, for example, but not limited to, REEMAY™ (Reemay, Inc.), and TYPAR™ (Reemay, Inc.). The housing can include a plurality of layers.

Typically, the housing 50 comprises one or more sheets of non-woven material that are secured (e.g., sealed) together. If desired, the housing can comprise a single sheet that is folded one or more times, before securing. The housing can be sealed, e.g., at the ends, sides, and to other components of the filter device and/or the set (such as, but not limited to, one of more components of the smoke filter, a conduit, a connector, a manifold, or a port), utilizing an adhesive, a solvent, radio frequency sealing, ultrasonic sealing and/or heat sealing. If desired, the housing can include any number of seals, with or without a seal to one or more components of the smoke filter and/or to the set.

In those embodiments wherein the smoke filter device includes a housing and a smoke filter, the smoke filter is associated with the housing to allow gas entering the device to pass through the filter and through the housing. In those embodiments wherein the smoke filter device does not include a housing (e.g., as shown in FIG. 6), the device is arranged to allow gas entering the device to pass through the smoke filter to the exterior of the device.

In accordance with these embodiments, the smoke filter comprises at least one porous smoke filter element comprising a hydrophobic retentive member, that typically comprises at least one microporous hydrophobic membrane and/or at least one hydrophobic depth filter medium. The embodiment of the filter device 300 illustrated in FIGS. 2–6 (as well as the embodiment of the filter device illustrated in FIG. 7b) has two smoke filters 100, 101, each comprising a porous smoke filter element 1, 11 comprising a hydrophobic retentive member. The porous smoke filter element can have one section or a plurality of sections and/or can comprise a plurality of layers. Alternatively, or additionally, the porous smoke filter element can comprise a plurality of media (e.g., at least one hydrophobic membrane and at least one fibrous hydrophobic medium).

Typically, the DOP smoke penetration rating of the smoke filter element 1, 11 is less than the rating for the odor-reducing element.

In those embodiments wherein the hydrophobic retentive member comprises at least one membrane, the pore structure (e.g., the pore rating, or the pore size) of the smoke filter element 1, 11 is typically less than the pore structure of the odor-reducing element. In some of those embodiments wherein the smoke filter element 1, 11 is not a depth filter (e.g., wherein the filter element does not provide prefiltration), the pore structure of the filter element is less than the pore structure of the separate prefiltration element.

The smoke filter element can be selected in accordance with several factors, including the nature and size of the undesirable materials in the smoke, the desired flow rate, and the acceptable pressure drop across the smoke filter.

In a preferred embodiment, the smoke filter element substantially prevents the passage therethrough of bacteria. In an even more preferred embodiment, the smoke filter element also substantially prevents the passage therethrough of viruses. For example, the embodiments of the smoke filter element can remove at least about 95% of the bacteria in the smoke, and provide at least about a 4 log viral reduction.

In more preferred embodiments, the smoke filter element can remove at least about 99% of the bacteria (in some embodiments, providing at least about 5 log bacterial reduction), and provide at least about a 5 log viral reduction.

In an even more preferred embodiment, the smoke filter element can remove essentially 100% of the bacteria (in some embodiments, providing at least about 7 log bacterial reduction), and provide at least about a 7 log viral reduction.

Typically, the smoke filter element removes at least about 99.97% of smoke particles having diameters of at least about 0.3 μm or greater, and more preferably, removes at least about 99.999%, or more, (for example, at least about 99.9995%) of smoke particles having diameters of at least about 0.12 μm. Illustratively, in one embodiment, smoke filter element has a DOP Smoke Penetration (e.g., as measured by ASTM D2986-71) at 0.3 μm at 10.5 ft/minute gas flow of at least about 0.03%, more preferably, at least about 0.015%.

Typically, in those embodiment wherein the smoke filter 40 element includes a membrane, the smoke filter element 1, 11 has a pore rating (e.g., as evidenced by bubble point) of about 10 micrometers or less, more preferably, about 5 micrometers or less, and even more preferably, about 2 micrometers or less.

Without being held to any particular mechanism, it is believed that small particles such as bacteria and viruses are removed by the smoke filter element by diffusion, including strong intermolecular forces (i.e., van der Waals' forces) even the element may have pores of a size larger than the size of the particles (free particles, or particles suspended in a droplet). Additionally, particles, including larger particles, can be removed by at least one of straining, inertial impaction and/or interception.

Typically, the effective filter area for the smoke filter(s) is at least 12.9 cm$^2$ (about 2 in$^2$), more preferably, at least about 19.4 cm$^2$ (about 3 in$^2$). In some embodiments, the effective filter area is about 22.6 cm$^2$ (about 3.5 in$^2$) or more, e.g., in the range of about 32.3 cm$^2$ to about 51.6 cm$^2$ (about 5 in$^2$ to about 8 in$^2$), or more.

The smoke filter element may be produced from any suitable natural and/or synthetic material capable of forming a substrate, fibers or a membrane that is compatible with the gas and smoke. In some embodiments, commercially available materials are preferred. Suitable polymers include, but are not limited to, polytetrafluoroethylene (PTFE), any nylon, e.g., 6, 6T, 11, 46, 66, and 610, polyvinylidene difluoride (PVDF), polyethersulfone (PES), polypropylene, and polyester.

Other suitable materials include cellulosic derivatives. Non-resinous materials, such as glass fibers, including microglass and/or laminated glass, can also be used.

Commercially available media, such as those available from Pall Corporation (East Hills, N.Y.) under the trademarks SUPOR®, and PALLFLEX®, are also suitable. Other suitable commercially available media include, but are not limited to, H&V HOVOGLAS™ (Hollingsworth & Vose Company, East Walpole, Mass.) and VERIFLO™ (Enhanced Filter, Ventura, Calif.).

The smoke filter element may remain untreated, or may be treated to increase its effectiveness. Surface characteristics of the element can be modified (e.g., to affect the CWST, to include a surface charge, e.g., a positive or negative charge, and/or to alter the polarity or hydrophilicity of the surface) by chemical reaction including, for example, wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, heat, a Van der Graff generator, ultraviolet light, electron beam, or to various other forms of radiation, or by surface etching or deposition using a plasma treatment. The smoke filter element can be initially hydrophilic, and treated to be made hydrophobic, and/or the smoke filter element can be treated to increase its hydrophobicity (i.e., to make it more hydrophobic).

The smoke filter element can have a variety of configurations. For example, the element can be substantially planar, pleated, corrugated, or cylindrical.

As noted earlier, the smoke filter 100, 101 can include additional components such as additional elements. For example, the smoke filter can include one or more upstream and/or downstream elements, such as a prefilter element, an odor-reducing element, as well as support and/or drainage elements. In some embodiments, at least a portion each of the elements of the smoke filter is flexible, e.g., pliant.

The smoke filter can comprise a composite, e.g., wherein one or more components is secured, e.g., laminated, to the smoke filter element. Alternatively, or additionally, the additional elements can be separate from the smoke filter.

Preferably, the smoke filter also includes an odor-reducing element. The smoke filter may also include a prefilter element, or the retentive member can provide retention and prefiltration (e.g., the retentive membrane can comprise a plurality of depth filter elements and/or fibrous layers).

In the illustrative embodiments shown in FIGS. 2–5, and 7b, the smoke filter also includes an odor-reducing element 3, 33, disposed downstream of the hydrophobic member (FIGS. 2–4, 7b) or upstream of the hydrophobic member (FIG. 5). The illustrative embodiment shown in FIG. 6 does not include an odor-reducing element.

Figure 2:
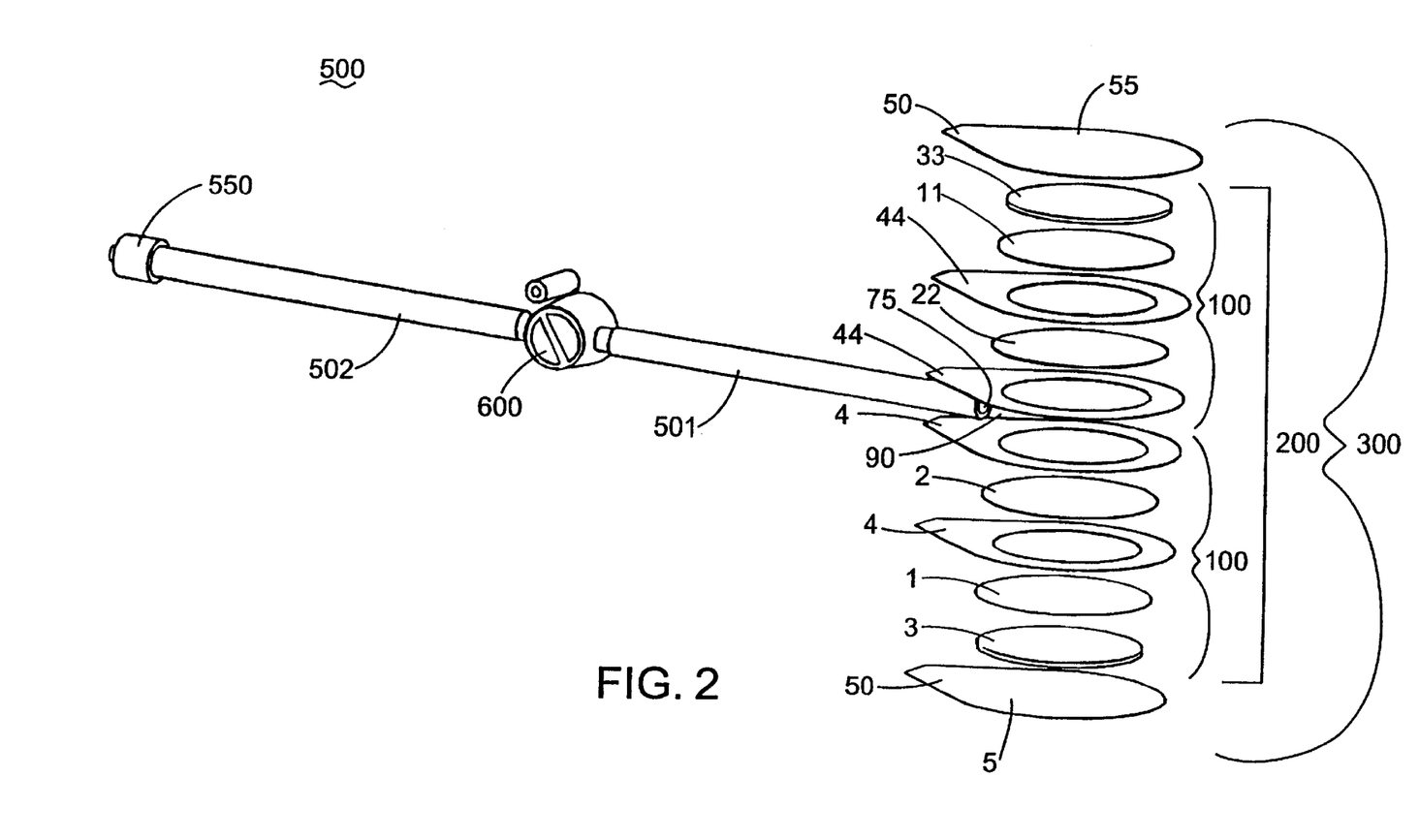
FIG. 2 is an exploded view of an embodiment of a smoke filter device including a smoke filter arrangement according to the present invention.
Figure 3:
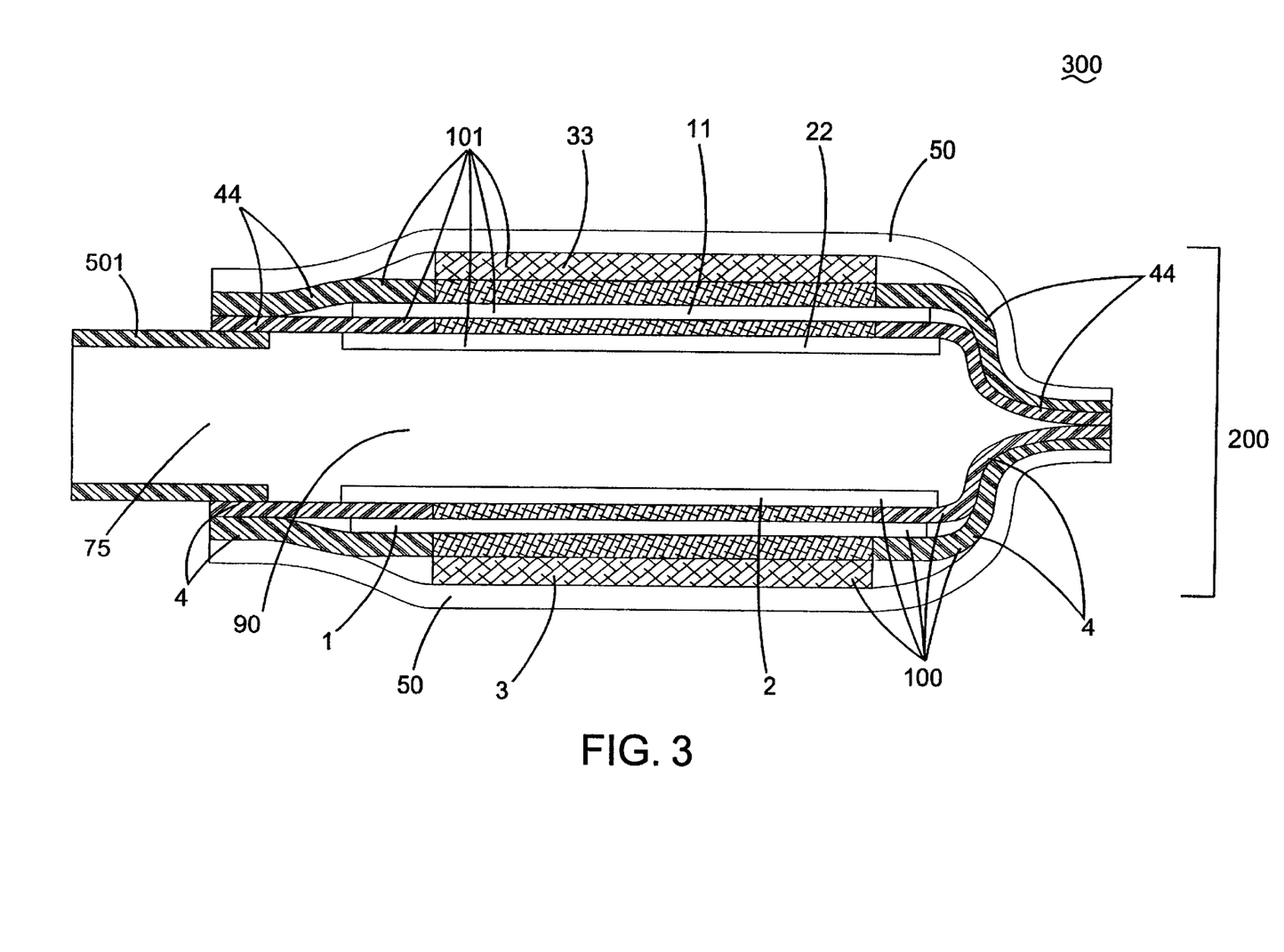
FIG. 3 is a cross-sectional view of the embodiment illustrated in FIG. 1, along line 3—3, including the smoke filter arrangement illustrated in FIG. 2.

The embodiment illustrated in FIGS. 2 and 3 includes prefilter elements 2, 22 and odor-reducing elements 3, 33. Either of these elements can include a plurality of layers. Preferably, the prefilter element and the odor-reducing element are very open and have good porosity. The prefilter element and odor reducing element can comprise any suitable woven or non-woven material, and can be formed from natural and/or synthetic material, e.g., fibers, polymeric material and/or glass. Exemplary materials include polypropylene, polyester, polyethersulfone, carbon (preferably activated carbon, e.g., charcoal and/or novoloid fibers) and/or microglass. Carbon can be granular and embedded in a matrix, or fibers mixed in a blend (e.g., a cotton/cellulose blend).

In some embodiments including a separate prefilter element, the prefilter element comprises a fibrous medium, e.g., including polymeric fibers and/or glass fibers.

In some embodiments including an odor-reducing element, the odor-reducing element also reduces the passage therethrough of undesirable substances such as other chemical matter and/or organic vapors. For example, in one illustrative embodiment including an odor-reducing element, the element may reduce the passage therethrough at least one of benzene, formaldehyde, hydrogen cyanide, and toluene.

In one preferred embodiment, the odor-reducing element comprises a carbon medium, preferably an activated carbon medium, even more preferably an activated fibrous carbon medium. One example of a suitable commercially available medium is the activated charcoal ULTRASORB™ (Enhanced Filter, Ventura, Calif.), e.g., as a fibrous or granulated laminate. Another example of a suitable commercially available medium is AQF® media (AQF Technologies, Charlotte, N.C.), e.g., activated carbon in a three dimensional polyester non-woven structure.

Typically, in those embodiments including an odor-reducing element, the odor-reducing element is downstream of the hydrophobic retentive member, i.e., gas passes through the retentive member before passing through the odor-reducing element. However, in some embodiments, e.g., as shown in FIG. 5, the odor-reducing element can be upstream of the hydrophobic retentive member, and can be the first element in the smoke filter.

In some embodiments, the smoke filter 100, 101 also includes one or more window elements, e.g., window elements 4, 44 as shown in FIGS. 2–6 and 7b. One or more window elements can have one or more windows or openings. The embodiments of the window elements 4, 44 shown in the Figures have one window or opening.

The window elements and windows can be of any suitable number, size and/or shape (e.g., rectangular, circular, triangular, oval). The smoke filter can include a plurality of window elements having different characteristics (e.g., shape, size and/or number of windows), and a window element can have a plurality of windows of different characteristics.

In a typical embodiment, at least one window element provides surface area for securing elements of the smoke filter together and/or for securing the filter to the A housing. For example, in the embodiments illustrated in FIGS. 2, 3, 6, and 7b, window elements secured to the smoke filter element 1, 11, and the prefilter element 2, 22, allow these elements to be sealed together. In accordance with the embodiment illustrated in FIGS. 2 and 3, the window elements also allow the smoke filter to be sealed to the inner surface of the side walls of the housing (with the odor-reducing element interposed between the smoke filter element and the side wall). In accordance with the embodiment illustrated in FIG. 7B, the window elements can also be secured to the manifold 700.

The window elements can also allow the inlet to be sealed to the housing. The widow elements can be secured to, for example, either of the opposing surfaces of a smoke filter element or a prefilter element. Securing, e.g., sealing, can include, for example, utilizing an adhesive, a solvent, radio frequency sealing, ultrasonic sealing and/or heat sealing. In some embodiments, e.g., some embodiments providing a subcomponent or subassembly of the filter device including carbon media, radio frequency sealing may be less desirable.

Typical materials suitable for producing the window element(s) include, but are not limited to, for example, plasticized polyvinyl chloride (PVC), polyester, polyurethane, polycarbonate, polypropylene, polyolefin, polyethylene, ethylene vinyl acetate (EVA), and combinations of materials.

In accordance with the invention, embodiments of the smoke filter device can be used in any medical protocol that involves venting gas from a patient's body cavity, and can be used with any suitable gas flow rate. The gas flow rate can be constant or variable, and can range from low flow rates, e.g., about 0.5 liters/min or less, or up to about 15 liters/min, or even more. In some embodiments, e.g., some embodiments of a smoke filter set including the smoke filter device, the set also includes a gas flow control device such as a valve, closure or clamp (including a screw clamp or pinch clamp). In some embodiments, the flow control device can be operated with one hand. If desired, the flow control device can be adjustable.

The smoke filter device is especially useful in those protocols that involve the production of smoke (e.g., created by a laser, electrocautery device, or an ultrasonic tissue fragmentation device). Typically, the device is capable of filtering smoke for up to about 6 minutes of cumulative. cauterization, or more, with a reduction in gas flow of about 50% or less. In some embodiments, the device is capable of filtering smoke for up to about 6 minutes of cumulative cauterization, or more, with a reduction in gas flow of about 40%, or less, e.g., about 30%, or less. In an embodiment, the device is capable of filtering smoke for up to about 6 minutes of cumulative cauterization, or more, with a reduction in gas flow of about 20% or less.

In accordance with an embodiment of the invention, a smoke filter device can deplete at least one chemical from (e.g., in, or associated with) the smoke, e.g., to provide an exposure limit that is equal to or less than the OSHA standard. Illustrative chemicals present in smoke, and exposure limits include those listed in *Surgical Smoke: What We Know Today* (Valleylab Inc., Boulder, Colo., copyright 1996), e.g., as listed in "Table 5: Chemicals, Exposure Limits, and Associated Health Effects" (page 12). For example, an embodiment of the smoke filter can deplete at least one of the following chemicals from smoke: acetaldehyde, acrolein, acetonitrile, benzene, hydrogen cyanide, carbon monoxide, formaldehyde, polyaromatic hydrocarbons (PAHs), styrene, toluene, and xylene.

Embodiments of the smoke filter device according to the invention can have any number of smoke filters, e.g., a single smoke filter, two smoke filters, or more than two smoke filters, and the smoke filter device can include a housing, or lack a housing. A portion of a smoke filter (e.g., a surface of the filter) can provide a portion of a side or an end of the smoke filter device. Alternatively, or additionally, an embodiment of the smoke device can include a housing having at least one portion (e.g., a portion of least one side wall) that is flexible and allows gas to pass therethrough, wherein the device is arranged to allow gas to pass through the smoke filter and the flexible portion of the housing.

In yet another embodiment, the housing is substantially inflexible, and/or the smoke filter is substantially inflexible. The housing may include one or more open portions (e.g., on at least one side of the device) that allow gas to pass through a flexible or inflexible smoke filter and through the open portion(s) of the device. Alternatively, or additionally, the smoke filter device can include a substantially inflexible housing, and can be arranged to allow the smoke filter to flex in the housing during use.

EXAMPLE 1

Figure 1:
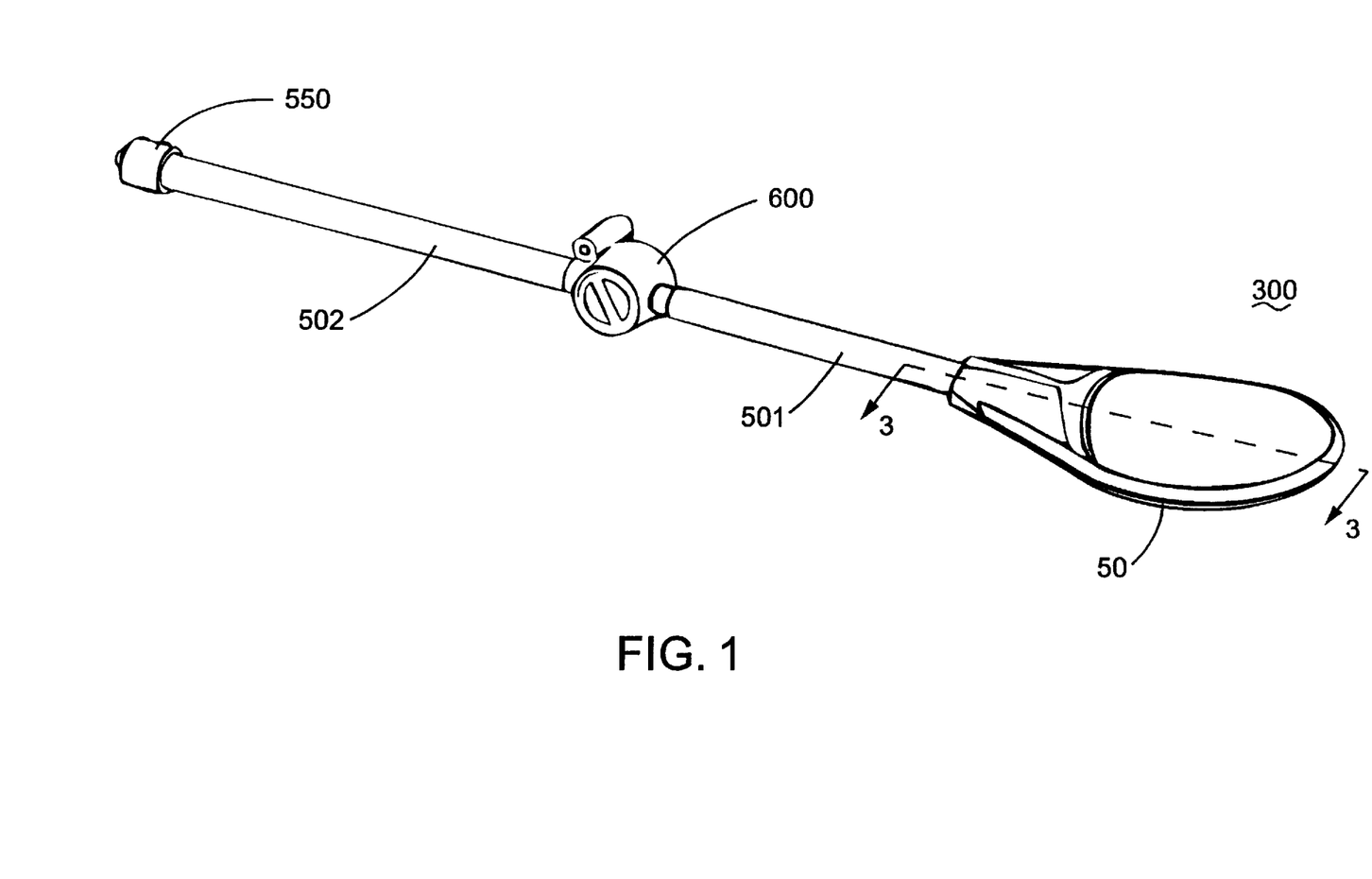
FIG. 1 is a perspective view of an embodiment of an assembled smoke filter device.

A smoke filter device is prepared with the configuration as generally shown in FIGS. 1–3. Each filter element disc has an effective diameter of 2.25 inches. The smoke filter elements are PTFE membranes that remove at least 99.999% of smoke particles having diameters of at least 0.10 $\mu$m or greater at 20 Liters/minute gas flow. The prefilter elements are H&V HOVOGLAS™ (Hollingsworth & Vose Colo.) fiber elements, and the odor-reducing elements are ULTRA-SORB™ (Enhanced Filter) activated carbon fibers (grade ACF-200) with a basis weight of 200 g/m². The window elements are PVC sheets, that have been cut to provide a central window with a diameter of 2.25 inches. The housing is REEMAY™ (Reemay, Inc.) non-woven media. The conduit is flexible PVC tubing.

The elements and housing are sealed together to provide a central cavity, bounded by the prefilter elements. The flexible tubing is inserted into the housing and sealed thereto. The filter device, that is pliable, is arranged to allow gas passing through the tubing into the central cavity to pass through the downstream prefilters, and subsequently through the smoke filter elements, the odor-reducing elements, and the side walls of the housing.

The smoke filter device is connected to a one-handed adjustable gas flow device, an additional conduit, and a luer fitting, that is subsequently connected to a trocar during a laparoscopic cholecystectomy (gall bladder removal). The $CO_2$ gas flow (when frequent cauterization begins) is 11 liters/min, and after 6 minutes cumulative electrocauterization, the gas flow remains well over 10 liters/min (i.e., the decrease in gas flow is less than 10%) at a constant pressure of 15 mm Hg (0.29 psi). The surgeon's vision is not obstructed by smoke in the abdominal cavity and there is no need to stop the procedure and vent smoke from the abdomen. There is no noticeable odor in the gas passing through the smoke filter device.

This example shows that a smoke filter device according to the invention is suitable for use in filtering smoke during electrocauterization.

EXAMPLE 2

A smoke filter device is prepared as described in Example 1.

The smoke filter device is connected to a one-handed adjustable gas flow device, an additional conduit, and a luer fitting, that is subsequently connected to a trocar during a laparoscopic cholecystectomy (gall bladder removal). The $CO_2$ gas flow (when frequent Harmonic Scalpel™ use begins) is 11 liters/min, and after 9 minutes cumulative harmonic scalpel use, the gas flow remains over 9 liters/min (i.e., the decrease in gas flow less than 20%) at a constant pressure of 15 mm Hg (0.29 psi). The surgeon's vision is not obstructed by aerosol in the abdominal cavity, and there is no need to stop the procedure and vent aerosol from the abdomen. There is no noticeable odor in the gas passing through the smoke filter device.

This example shows that a smoke filter device according to the invention is suitable for filtering smoke and for use with a Harmonic Scalpel™ device.

EXAMPLE 3

This example is designed to show whether smoke filter devices according to the invention can remove volatile organic chemicals in cautery smoke.

Three embodiments of smoke filter devices are prepared and tested. The first device is prepared as generally described in Example 1, but without a flow control device and an extra conduit. The second device is prepared in a similar configuration; however, the odor-reducing elements are AQF® media 2750 (AQF Technologies, Charlotte, N.C.) having a basis weight of 600 g/m², rather than the ULTRASORB™ media utilized in Example 1.

The third device has a configuration as generally shown in FIG. 4, wherein each smoke filter element has two H&V HOVOGLAS™ fiber elements, and the odor-reducing elements are ULTRASORB™ activated carbon fibers (grade ACF-200) with a basis weight of 200 g/m². The device does not include a membrane. The window elements, housing (and sealing thereof), as well as the conduit, are as described in Example 1.

The smoke filter devices are separately connected to a test chamber. The test chamber includes a lid having two trocar sleeve access ports. A carbon dioxide canister is connected to an insufflator, and an insufflation tubing set connects the insufflator to the chamber.

A first trocar is used to pass the cautery scalpel through a trocar sleeve access port into the chamber to create smoke, and the other trocar sleeve access port is used as a collection port for either a filtered sample, or a control sample. The filter device is attached via the second trocar to the collection port. For each test, a prepared tube treated with Tenax TA polymer resin (Scientific Instrument Services, Ringoes, N.J.) is placed downstream of the filter device to absorb the substances of interest, and the polymer treated tube will be disconnected and the resin desorbed to quantify the substance of interest. The tubes are prepared for quantifying the following substances: 3-methyl-2-butenal, benzene, styrene, toluene, and ethyl benzene.

Beef liver is placed on a grounding plate in the test chamber, and the chamber is sealed. The insufflator is turned on and set for 15 mm Hg at a maximum fill rate of 40 Liters/min. The trocar ports are closed via a stopcock. A 10 second cautery burst clouds the chamber, and 6 bursts are created to provide a cumulative total of 1 minute of smoke. After each burst, the trocar stopcocks are opened, allowing gas to flow through the ports and the filter device for about 30 seconds. The stopcocks are then closed. After recording the total gas flow through the insufflator, the polymer treated tube is disconnected and stored for desorption.

The filter device is then removed, and a control tube is attached. Another minute of smoke is provided and passed through the ports as described previously, and the polymer treated tube is disconnected and stored for desorption.

The filter device is then reconnected (without a polymer treated tube), and another minute of smoke is passed through the filter. The chamber is then cleared, and a polymer treated tube is connected. Another minute of smoke is provided as described previously (for a cumulative total of 3 minutes of smoke), and the tube is disconnected and stored and desorption.

The filter device is then removed, and another control tube is attached. Another minute of smoke is provided as described previously, and the tube is disconnected and stored for desorption.

The above-described process, i.e., with a filter, and with a control (without a filter), is repeated, using a new filter to test each substance of interest.

The results are provided in the following Table:

TABLE

Removal Efficiency (Units = Nanograms)

|  | Minute 1 | Minute 3 | Control | Average % |
|---|---|---|---|---|
| 3-Methyl-2-Butenal | | | | |
| First Device | 0 | 0 | 35 | 100.0 |
| Second Device | 0 | 0 | 23 | 100.0 |
| Third Device | 0 | 0 | 42 | 100.0 |
| Benzene | | | | |
| First Device | 17 | 17 | 460 | 96.3 |
| Second Device | 31 | 10 | 440 | 95.3 |
| Third Device | 57 | 62 | 390 | 84.7 |
| Styrene | | | | |
| First Device | 0 | 0 | 110 | 100.0 |
| Second Device | 0 | 0 | 120 | 100.0 |
| Third Device | 0 | 18 | 0 | not applicable |
| Toluene | | | | |
| First Device | 14 | 39 | 420 | 93.7 |
| Second Device | 28 | 23 | 470 | 94.6 |
| Third Device | 47 | 63 | 640 | 91.4 |
| Ethyl Benzene | | | | |
| First Device | 0 | 104 | 104 | 50.0 |
| Second Device | 0 | 28 | 110 | 87.3 |
| Third Device | 183 | 0 | 210 | 56.4 |

With respect to 3-methyl-2-butenal in particular, that is believed to be a substance responsible for a significant portion of the foul odor produced during cauterization, the smoke filter devices deplete 3-methyl-2-butenal to below detectable levels in both the first and third minute of exposure, whereas the control levels range from 23 ng to 42 ng. Odor is not detected in the filtered samples, whereas odor is detected in each of the control samples.

As shown in the Table, in addition to depleting 3-methyl-2-butenal, these embodiments of smoke filter devices reduced the levels of the following organic substances: benzene, styrene, and toluene.

This example shows smoke filter devices according to the invention remove organic volatiles, including some of the volatiles thought to be responsible for a portion of the foul odor produced during cauterization.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A smoke filter device for use with positive pressure during a medical procedure comprising;
   a filter housing having an interior cavity, the housing having at least a first side wall and an opposing second side wall, the first and second side walls each having at least a portion that is flexible and allows gas to pass therethrough; and
   a smoke filter capable of filtering smoke from gas comprising at least a first porous filter element and a second porous filter element, the first and second filter elements each comprising a hydrophobic retentive member;
   wherein the filter device is arranged to allow gas to pass into the interior cavity, through the first porous filter element, and through the first side wall of the housing.

2. The smoke filter device of claim 1, wherein the smoke filter device is arranged to allow gas to pass into the interior cavity, through the second porous filter element, and through the second side wall of the housing.

3. The smoke filter device of claim 1, wherein the first side wall of the housing and the second side wall of the housing each comprise a non-woven medium.

4. The smoke filter device of claim 2, further comprising a first odor-reducing element comprising a carbon medium and a second odor-reducing element comprising a carbon medium.

5. The smoke filter device of claim 3, further comprising a first odor-reducing element comprising a carbon medium and a second odor-reducing element comprising a carbon medium.

6. The smoke filter device of claim 1, wherein the first and second porous filter elements each have an effective filtration area of at least about 12.9 cm$^2$.

7. The smoke filter device of claim 6, wherein the first porous filter element is sealed to the first side wall of the housing comprising a non-woven medium and the second porous filter element is sealed to the second side wall of the housing comprising a non-woven medium.

8. The smoke filter device of claim 4, wherein the first porous filter element is adjacent to the first odor-reducing element, and the second porous filter element is adjacent to the second odor-reducing element.

9. The smoke filter device of claim 2, wherein the first porous filter element and the second porous filter element each comprise a membrane.

10. The smoke filter device of claim 2, further comprising a first window element sealed to the first side wall of the housing and a second window element sealed to the second side wall of the housing.

11. The smoke filter device of claim 2, further comprising an inlet port and a conduit communicating with the port.

12. The smoke filter device of claim 3, wherein the filter device is capable of filtering smoke for up to about 6 minutes of cumulative smoke with a reduction in gas flow of about 50% or less from an initial gas flow of 11 liters/min at a constant pressure.

13. A smoke filter set comprising the smoke filter device of claim 11, further comprising a gas flow control device for controlling the flow of gas into the smoke device, communicating with the conduit.

14. A smoke filter device for use with positive pressure during a medical procedure comprising:
   a filter housing having an inlet port and an interior cavity, the housing having at least a first side wall and a second side wall, the first and second side walls each comprising a non-woven medium; and
   a smoke filter capable of filtering smoke from gas comprising at least a first porous filter element and a first odor-reducing element, and a second porous filter element and a second odor-reducing element, the first and second filter elements each comprising a hydrophobic retentive member, and the first and second odor-reducing elements each comprising an activated carbon medium;
   wherein the filter device is arranged to allow gas to pass through the inlet port into the interior cavity, through the first porous filter element, the first odor-reducing element and through the first side wall of the housing, and through the second porous filter element, the second odor-reducing element and through the second side wall of the housing.

15. The smoke filter device of claim 14, wherein the first and second porous filter elements each comprise a membrane.

16. The smoke filter device of claim 14, wherein the first and second porous filter elements each have an effective filtration area of at least about 12.9 cm$^2$.

17. A smoke filter device for use with positive pressure during a medical procedure comprising:
   a filter housing having an inlet port and an interior cavity, the housing having a first side wall and a second side wall, the first and second side walls each comprising a non-woven medium;
   a first smoke filter adjacent the first side wall, the first smoke filter comprising a first porous filter element comprising a hydrophobic retentive member;
   a prefilter element and/or an additional element comprising a carbon medium, the prefilter element and/or the additional element in fluid communication with the first smoke filter;
   a second smoke filter adjacent the second side wall, the second smoke filter comprising a second porous filter element comprising a hydrophobic retentive member;
   a prefilter element and/or an additional element comprising a carbon medium, the prefilter element and/or the additional element in fluid communication with the second smoke filter,
   wherein the filter device is arranged to allow gas to pass through the inlet port into the interior cavity, through the first smoke filter and through the first side wall of the housing, and through the second smoke filter and through the second side wall of the housing.

18. The smoke filter device of claim 17, wherein the first porous filter element and the second porous filter element each comprise a membrane, and the prefilter element in communication with the first smoke filter and the prefilter element in communication with the second smoke filter each comprise a fibrous medium.

19. A method for removing smoke during surgery comprising:

creating smoke during surgery, and passing the smoke by positive pressure through the smoke filter device of claim 2 to provide a smoke-depleted gas.

20. A method for filtering gas using positive pressure during a medical procedure comprising:

passing gas used in a medical procedure through a gas filter device comprising a housing having an inlet port, an interior cavity, a first side wall and a second side wall, wherein at least a portion of the first and second side walls allows gas to pass therethrough;

wherein the device includes a gas filter adapted to filter smoke from gas comprising at least a first porous filter element and a second porous filter element, the interior cavity of the device being between the first and second filter elements, the first and second filter elements each comprising a hydrophobic retentive member;

wherein the filter device is arranged to allow gas to pass through the inlet port into the interior cavity, through the gas filter comprising the first and second porous filter elements, and through the first and second side walls of the housing.

21. The method of claim 5, wherein passing gas through the gas filter includes passing gas through the first porous filter element and a first odor-reducing element comprising a carbon medium, and passing gas through the second porous filter element and a second odor-reducing element comprising a carbon medium.

22. The method of claims 5, wherein passing gas through the filter device includes depleting smoke from the gas.

23. The method of claim 7, wherein passing gas through the filter device includes reducing the level of at least one chemical in the gas.

24. The method of claim 22, wherein passing gas through the filter device includes removing aerosol from the gas.

25. The method of claim 21, wherein passing gas through the filter device includes removing aerosol from the gas.

26. A method for filtering smoke using positive pressure during a medical procedure comprising:

passing gas into a body cavity of a patient, and passing smoke-containing gas from the body cavity into a smoke filter device comprising a housing having at least a first side wall and a second side wall, wherein the first and second side walls each comprise a non-woven medium, and the device includes a smoke filter adapted to filter smoke comprising at least a first porous filter element and a first odor-reducing element, and a second porous filter element and a second odor-reducing element, the first and second filter elements each comprising a hydrophobic retentive member, and the first and second odor-reducing elements each comprising an activated carbon medium;

passing the smoke-containing gas through the smoke filter and passing smoke-depleted gas through the first and second side walls of the housing.

27. The smoke filter device of claim 17, wherein the first smoke filter comprises a first porous element comprising a hydrophobic retentive member, a prefilter element and an additional element comprising a carbon medium; and the second smoke filter comprises a second porous element comprising a hydrophobic retentive member, a prefilter element and an additional element comprising a carbon medium.

28. The smoke filter device of claim 14, wherein the first porous filter element is sealed to the first side wall of the housing comprising a non-woven medium and the second porous filter element is sealed to the second side wall of the housing comprising a non-woven medium.

29. The smoke filter device of claim 14, wherein the first porous filter element is adjacent to the first odor-reducing element, and the second porous filter element is adjacent to the second odor-reducing element.

30. The smoke filter device of claim 14, further comprising a first window element sealed to the first side wall of the housing and a second window element sealed to the second side wall of the housing.

31. The smoke filter device of claim 1, wherein each hydrophobic retentive member comprises a PTFE membrane.

32. The smoke filter device of claim 16, wherein the first and second porous filter elements each comprise a PTFE membrane.

33. The smoke filter device of claim 17, wherein the first and second smoke filter elements each comprise a PTFE membrane.

34. The smoke filter device of claim 33, wherein the first and second smoke filters each comprise a prefilter element and an additional element comprising an odor reducing element including activated carbon.

* * * * *